US008926566B2

(12) United States Patent
Ratjen

(10) Patent No.: US 8,926,566 B2
(45) Date of Patent: Jan. 6, 2015

(54) MEDICAMENT DELIVERY DEVICE

(75) Inventor: Jochen Ratjen, Nacka (SE)

(73) Assignee: SHL Group AB, Nacka Strand (SE)

( * ) Notice: Subject to any disclaimer, the term of this patent is extended or adjusted under 35 U.S.C. 154(b) by 284 days.

(21) Appl. No.: 13/641,105

(22) PCT Filed: Apr. 8, 2011

(86) PCT No.: PCT/SE2011/050427
§ 371 (c)(1),
(2), (4) Date: Oct. 23, 2012

(87) PCT Pub. No.: WO2011/133086
PCT Pub. Date: Oct. 27, 2011

(65) Prior Publication Data
US 2013/0204194 A1 Aug. 8, 2013

Related U.S. Application Data

(60) Provisional application No. 61/325,537, filed on Apr. 19, 2010.

(30) Foreign Application Priority Data

Apr. 19, 2010 (SE) ..................... 1050385

(51) Int. Cl.
A61M 5/20 (2006.01)
A61M 5/32 (2006.01)
A61M 5/00 (2006.01)
A61M 5/31 (2006.01)

(52) U.S. Cl.
CPC .............. A61M 5/31 (2013.01); A61M 5/2033 (2013.01); A61M 5/3129 (2013.01); A61M 5/3137 (2013.01); A61M 2005/3104 (2013.01)

USPC ........... 604/187; 604/131; 604/192; 604/227

(58) Field of Classification Search
CPC ....... A61M 5/2033; A61M 5/20; A61M 5/30; A61M 5/3129; A61M 5/3134; A61M 5/3135; A61M 5/3137; A61M 5/31566; A61M 5/31
USPC ......... 604/131, 134, 135, 181, 187, 192, 218, 604/227
See application file for complete search history.

(56) References Cited

U.S. PATENT DOCUMENTS 5,865,804 A * 2/1999 Bachynsky ................... 604/134
6,149,626 A * 11/2000 Bachynsky et al. ........... 604/134
(Continued)

FOREIGN PATENT DOCUMENTS

EP 2168621 A1 3/2010

OTHER PUBLICATIONS

Swedish Patent Office, Int'l Search Report in PCT/SE2011/050427, Jul. 19, 2011.

(Continued)

Primary Examiner — Matthew F Desanto
(74) Attorney, Agent, or Firm — Piedmont Intellectual Property

(57) ABSTRACT

Medicament delivery device comprising an elongated housing (10) comprising a grip member (64) connected to the elongated housing and movable between a rest position in which the device has a predetermined grip size and an operation position in which the pre-determined grip size of the device is increased for providing an improved grip of the device during use.

18 Claims, 8 Drawing Sheets

(56) References Cited

U.S. PATENT DOCUMENTS

| | | |
|---|---|---|
| 7,611,495 B1 | 11/2009 | Gianturco |
| 8,062,268 B2 * | 11/2011 | Ratjen ............................ 604/224 |
| 2004/0116856 A1 | 6/2004 | Woehr et al. |
| 2008/0214996 A1 * | 9/2008 | Kimmell et al. ................ 604/68 |

OTHER PUBLICATIONS

Swedish Patent Office, Written Opinion in PCT/SE2011/050427, Jul. 19, 2011.

* cited by examiner ion the present invention is characterized by

MEDICAMENT DELIVERY DEVICE

TECHNICAL AREA

The present invention relates to a medicament delivery device and in particular a device with improved grip abilities for users and an activation locking function.

BACKGROUND OF INVENTION

There is a large number of medicament delivery devices that have been invented and developed that are intended for self-medication by a patient or a user. In particular pen-like injectors have been developed where the intention is to have a device preferably displaying a number of automatic or semi-automatic functions such as mixing, priming, penetration, injection and/or withdrawal. From a patient's or user's point of view the device should be easy and intuitive to use and often at the same time with a reduced size so that it is easy to bring along and discrete when used. These different demands are not always so easy to combine in one device because an increased number of functions add to the necessary size of the device. On the other hand, for some patients the pen-shape is not ideal, especially for persons with reduced dexterity in the hands. The pen-shape is then difficult to grip in a secure and positive way. In those cases and for that type of patients, the device is then made with a form and size providing a better grip which then means that the size of the device increases and thus becomes more difficult to bring along and use in a discrete way.

One example of an "enlarged" device is disclosed in document WO 9810813, which also is on the market under the trade name InnoLet®. The device is developed for diabetes treatment of elderly with reduced strength where a dose setting is performed by turning a large dial similar to an egg-clock dial. Further the distal end of the device is arranged with a very large activation button in order to facilitate activation of the injection. The device is rather bulky and not so easy to bring along in for example a pocket.

It is also desirable that such devices possess a premature activation locking function until a cap has been removed and/or until a delivery member has been attached to the device.

Also, there is thus still a demand for a device that can provide a good and secure grip even for persons with reduced dexterity and/or strength of the hands and yet is small and easy to bring along.

BRIEF DESCRIPTION OF INVENTION

There is a main objective with the present invention to provide a medicament delivery device that does not display the drawbacks of the state of the art medicament delivery devices.

According to a main aspect of the invention it is characterised by a medicament delivery device comprising an elongated housing having opposite distal and proximal ends, comprising; a grip member connected to the elongated housing and movable between a rest position in which the device has a predetermined grip size and an operation position in which the pre-determined grip size of the device is increased for providing an improved grip of the device during use, wherein said grip member comprises an elongated arc-shaped rib arranged extending in the longitudinal direction of the device and being rotatably attached to the housing and wherein the housing is designed comprising opposite first and second surface parts, wherein the first surface part comprises an elongated arc-shape, and wherein the second surface part is generally parallel with the longitudinal axis of the device, such that when the rib is in the rest position, the first surface part and an inner surface of the rib are abutting each other such that the predetermined grip size of the device is the distance between the second surface part and an outer surface of the rib, and when the rib is in the operation position, the rib is positioned opposite to the first part surface such that the increased predetermined grip size is the distance between the outer surface of the rib and the first surface part.

According to another aspect of the invention said rib is arranged with limiting means arranged to co-act with corresponding limiting means of the housing.

According to yet another aspect of the invention the rib comprises a support member arranged to be in contact with said housing for preventing a radial movement of said rib when said rib is in the operation position and said device is gripped by a user.

According to a further aspect of the invention the medicament delivery device is an injection device.

According to yet a further aspect of the invention said housing is arranged to accommodate a medicament container.

According to another aspect of the invention said device further comprises actuation means and drive means interactively connected to each other, and wherein said drive means are arranged within said elongated housing and capable of, upon manual activation of said actuation means, acting on a movable stopper inside said medicament container for expelling a dose of medicament.

According to yet another aspect of the invention said device further comprises a hold and release means; wherein said hold and release means are interactively connected to the drive means for holding said drive means in a pre-tensioned state, and to the actuation means, such that when the actuation means are activated said hold and release means release the drive means from the pre-tensioned state.

According to a further aspect of the invention said actuation means is interactively connected to the rib and to the housing, and wherein said actuation means is movable between a locked position in which said actuation means and said housing are interlocked to each other by actuation interlocking means when the rib is in the rest position, and a released position in which said actuation means are released from said housing when the rib is in the operation position, such that the actuation button can be activated for interacting with the hold and release means and thereby release the drive means from the pre-tensioned state.

According to yet a further aspect of the invention said device further comprises a protective cap releasibly attached to the proximal end of the housing, operably connected to said rib and movable between a closed position in which said protective cap and said rib are interlocked to each other when said rib is in the rest position and an open position in which said protective cap is removed such that the rib can be moved from the rest position to the operation position.

According to another aspect of the invention said device further comprises a protective cap releasibly attached to the proximal end of the housing and operably connected to said rib, such that said protective cap and said rib are interlocked to each other when said rib is in the rest position and such that said protective cap and said rib are released from each other when said rib is in the operation position such that said cap can be removed.

There are a number of advantages with the present invention. Due to the grip member which is movable from a rest position to an operation position, the grip size can be enlarged at the moment when the device is to be used, thus providing an improved grip for the user. On the other hand, when the device is not in use, i.e. in rest position, the grip member is positioned in the rest position and the size of the device is almost as if no grip member was present.

The design of the longitudinally extending and curved rib gives a good size enlargement and improved grip with very little extra material. The use of a support member further enhances the improved grip of the device.

Another advantage with the grip member is the possibility of the extra function as a safety lock of the actuation means. In this aspect, when the locking and unlocking of the actuation means is performed by moving it, this action and the force required to do it is simplified and reduced respectively when the grip member is used for the rotation.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

In the present application, when the term "distal part/end" is used, this refers to the part/end of the medicament delivery device, or the parts/ends of the members thereof, which under use of the medicament delivery device is located the furthest away from the medicament delivery site. Correspondingly, when the term "proximal part/end" is used, this refers to the part/end of the medicament delivery device, or the parts/ends of the members thereof, which under use of the medicament delivery device is located closest to the medicament delivery site.

Figure 8:
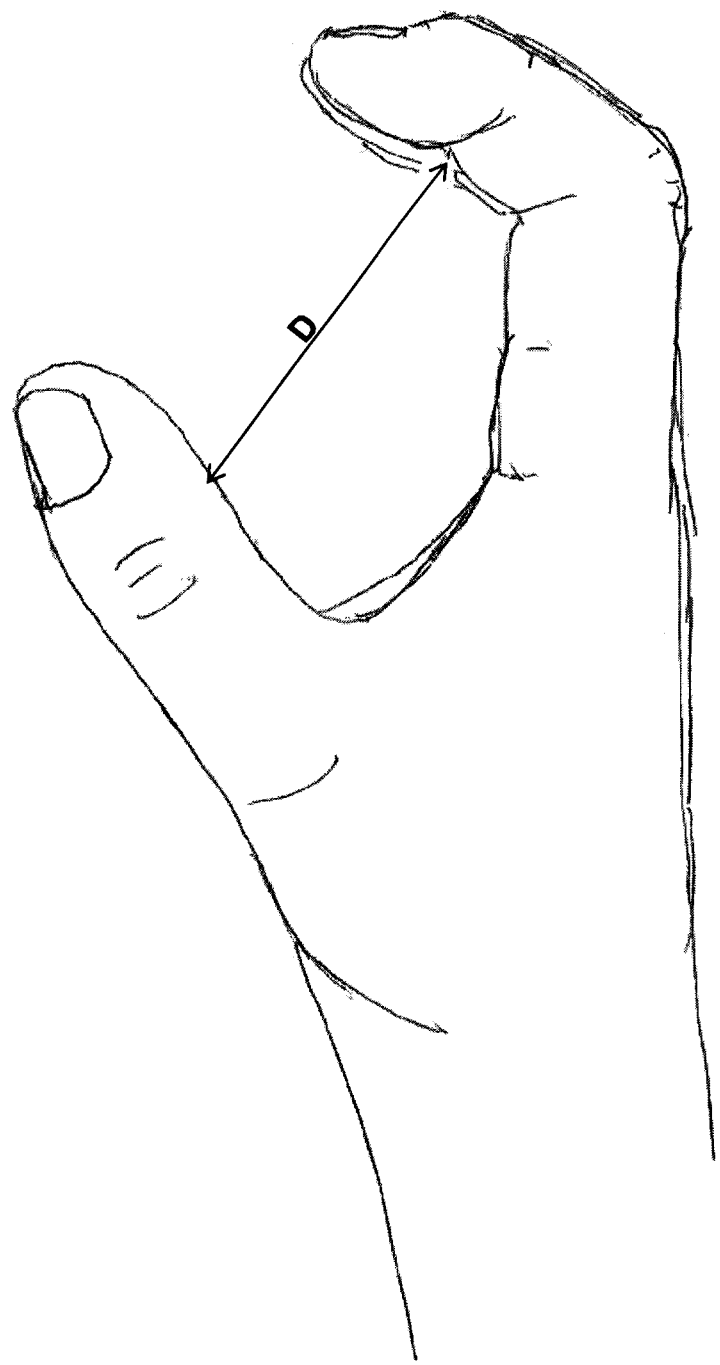
FIG. 8 is a view of a hand of a user for defining the grip size wording.

In the present application, the wording grip size is defined as the distance D between the thumb and the rest of the fingers of a users hand when an object is gripped. See FIG. 8. Consequently, the grip size of an object is the distance between two opposite surfaces of a grip area.

The medicament delivery device according to the invention comprises an elongated housing 10 having opposite distal 48 and proximal 12 ends; a grip member connected to the elongated housing and movable between a rest position in which the device has a predetermined grip size and an operation position in which the predetermined grip size of the device is increased for providing an improved grip of the device during use.

The grip member comprises an elongated arc-shaped rib 64 arranged extending in the longitudinal direction of the device and being rotatably attached to the housing. Said rib being arranged with limiting means arranged to co-act with corresponding limiting means of the housing.

The housing is designed comprising opposite first 74 and second 76 surface parts, wherein the first surface part comprises an elongated arc-shape, and wherein the second surface part is generally parallel with the longitudinal axis of the device, such that when the rib is in the rest position, the first surface part and an inner surface of the rib are abutting each other such that the predetermined grip size of the device is the distance between the second surface part and an outer surface of the rib, and when the rib is in the operation position, the rib is positioned opposite to the first part surface such that the increased predetermined grip size is the distance between the outer surface of the rib and the first surface part.

Further, the rib comprises also a support member 78 arranged to be in contact with said housing for preventing a radial movement of said rib when said rib is in the operation position and said device is gripped by a user.

Figure 1:
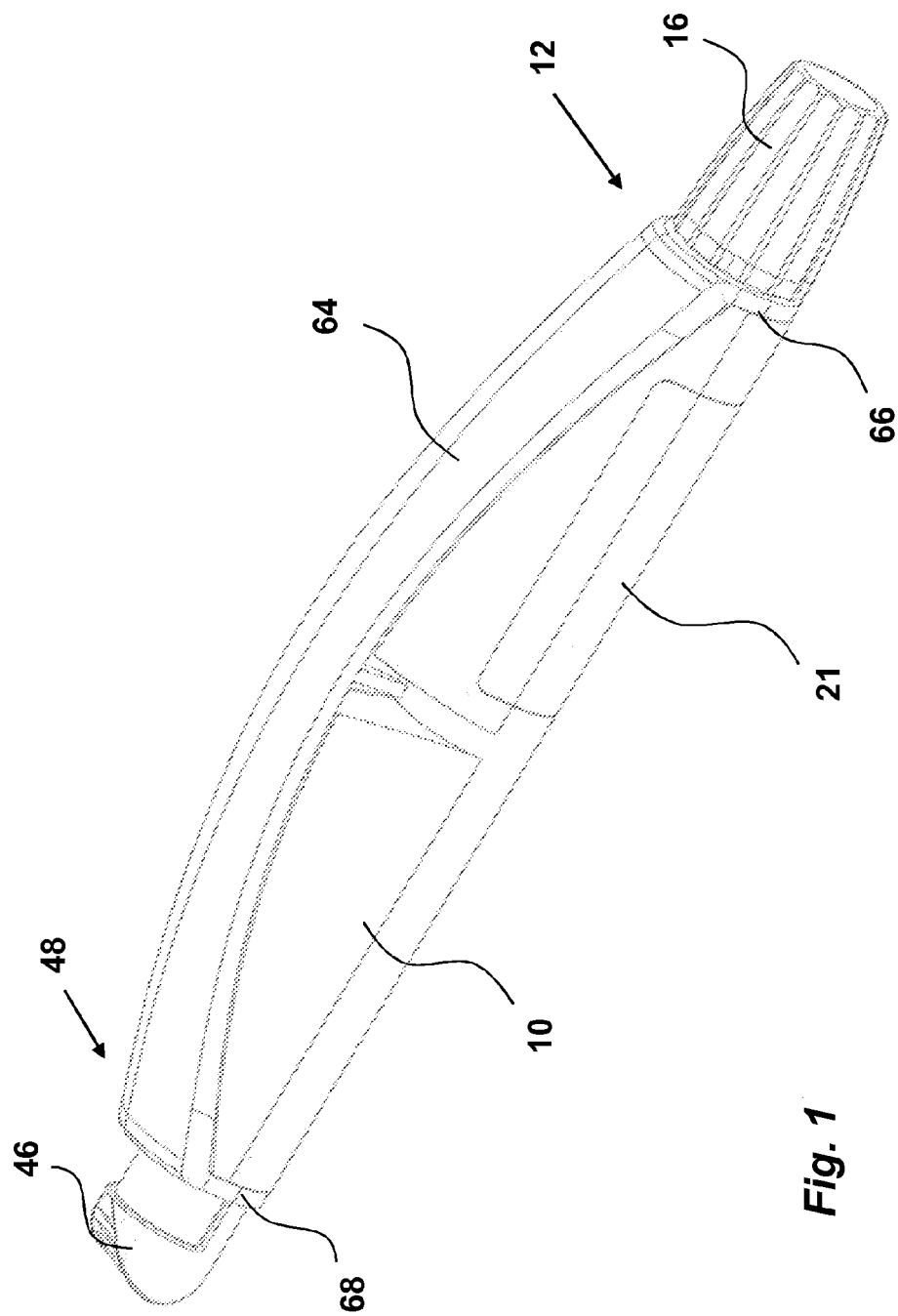
FIG. 1 is a perspective view of a medicament delivery device of the present invention in a rest position.

An exemplary embodiment but not restricted to it is shown in the FIGS. 1-7. The exemplary device is an injection device and more particularly an auto-injection device. The exemplary device comprises a generally elongated housing 10 having opposite distal 48 and proximal 12 ends. In FIG. 1 the exemplary embodiment is made by two halves. In this context it is to be understood that the housing may comprise more or less components for e.g. manufacturing and assembly reasons.

The housing is further arranged with a compartment intended to house a medicament container 18 containing medicament to be expelled through a medicament delivery member such as an injection needle, a mouth piece, a nozzle or the like. Inside the medicament container 18 a stopper 20 is arranged to be movable. The medicament container is preferably transparent and is visible via a transparent window 21 as a part of the housing 10. In this way the content of the medicament container is visible for a user.

The device further comprises drive means arranged within said elongated housing and capable of acting on the movable stopper 20 inside said medicament container 18 for expelling a dose of medicament, a hold and release means and an actuation means; wherein said hold and release means are interactively connected to the drive means for holding said drive means in a pre-tensioned state, and to the actuation means, such that when the actuations means are activated said hold and release means release the drive means from the pre-tensioned state.

It is to be understood that the device may only comprise actuation means and drive means interactively connected to each other, and wherein said drive means are arranged within said elongated housing and capable of, upon manual activation of said actuation means, acting on the movable stopper 20 inside said medicament container for expelling a dose of medicament.

Figure 2:
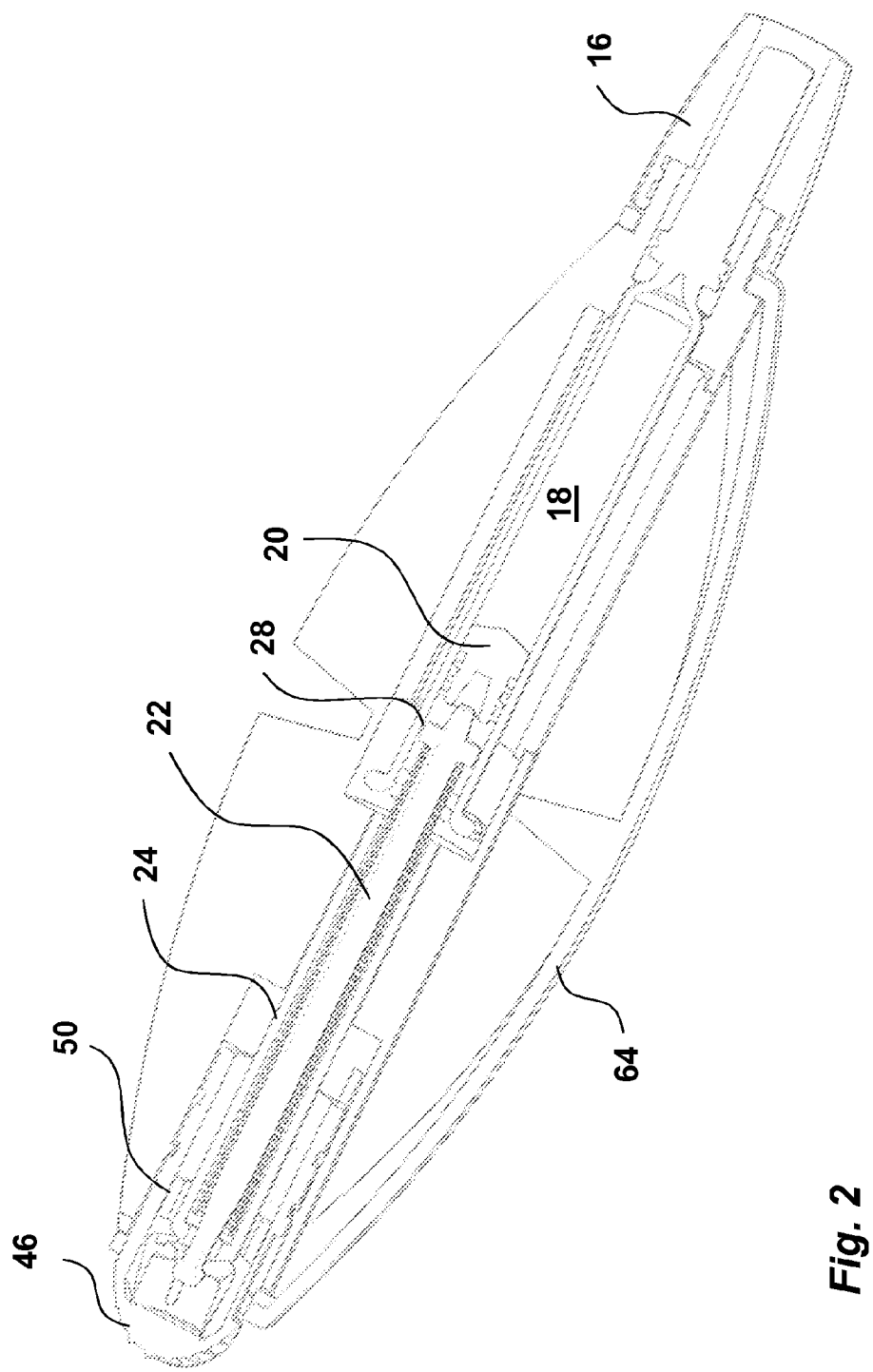
FIG. 2 is a cross-sectional view of the device of FIG. 1.
Figure 4:
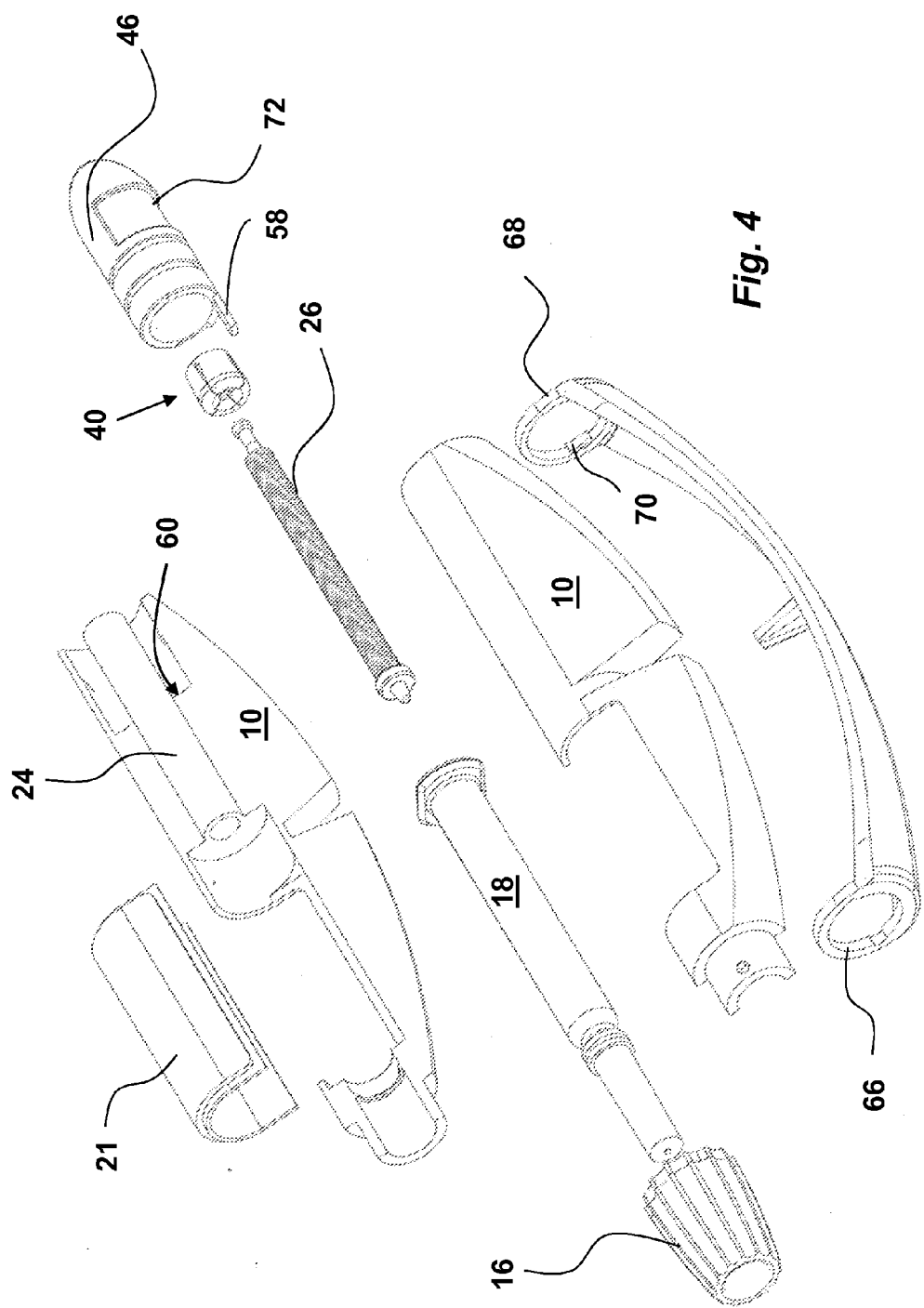
FIG. 4 is an exploded view according to FIG. 3 rotated 180 degrees.
Figure 5:
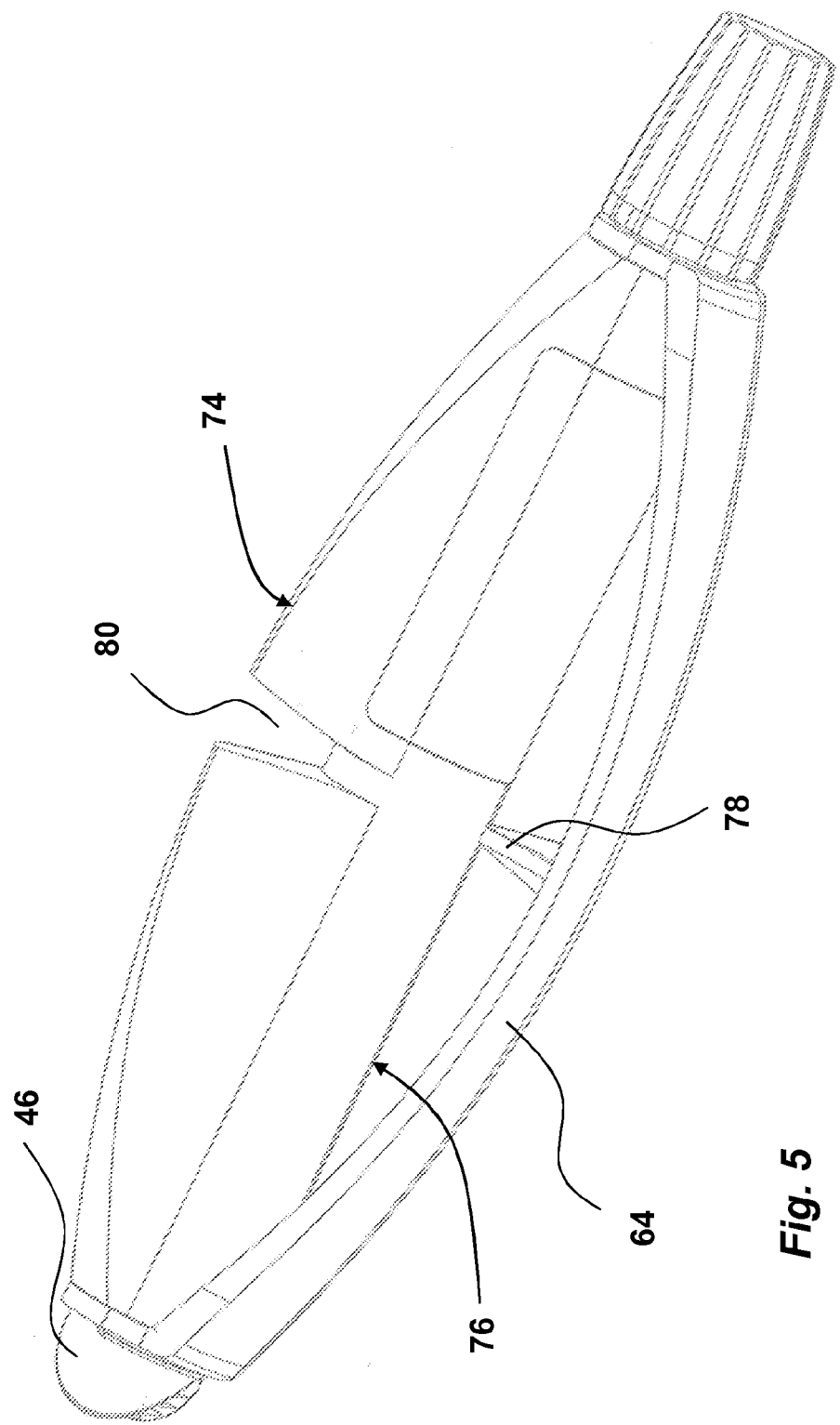
FIG. 5 is a perspective view according to FIG. 1 in an operation position.

The drive means of the exemplary embodiment are shown in FIG. 2 and comprise a plunger rod 22 and a resilient member as e.g. a compression spring arranged around the plunger rod. The plunger rod comprises a proximal end which is in contact with the stopper 20. The drive means are positioned in a tubular part 24 of the housing as seen in FIG. 4. The resilient member 26 is arranged between an annular ledge 28 at the proximal end of the plunger rod and an end wall 30 of the tubular part 24, FIGS. 2 and 6. The end wall 30 of the tubular part is further arranged with a central passage 32 through which distal end of the plunger rod 22 extends. A distally directed surface 34 of the end wall 30 is bevelled as seen in FIG. 6.

Figure 3:
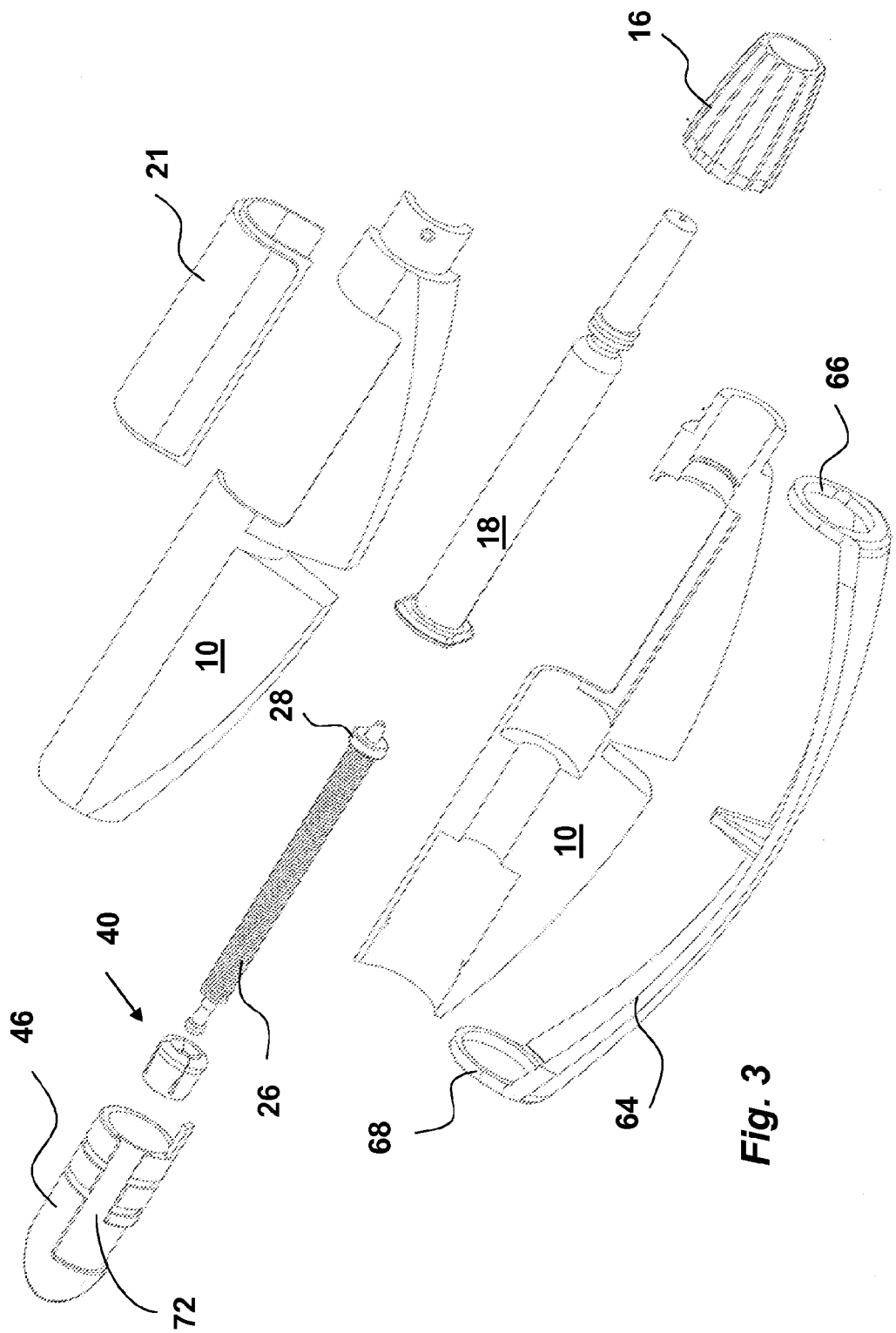
FIG. 3 is an exploded view of the device of FIG. 1.
Figure 6:
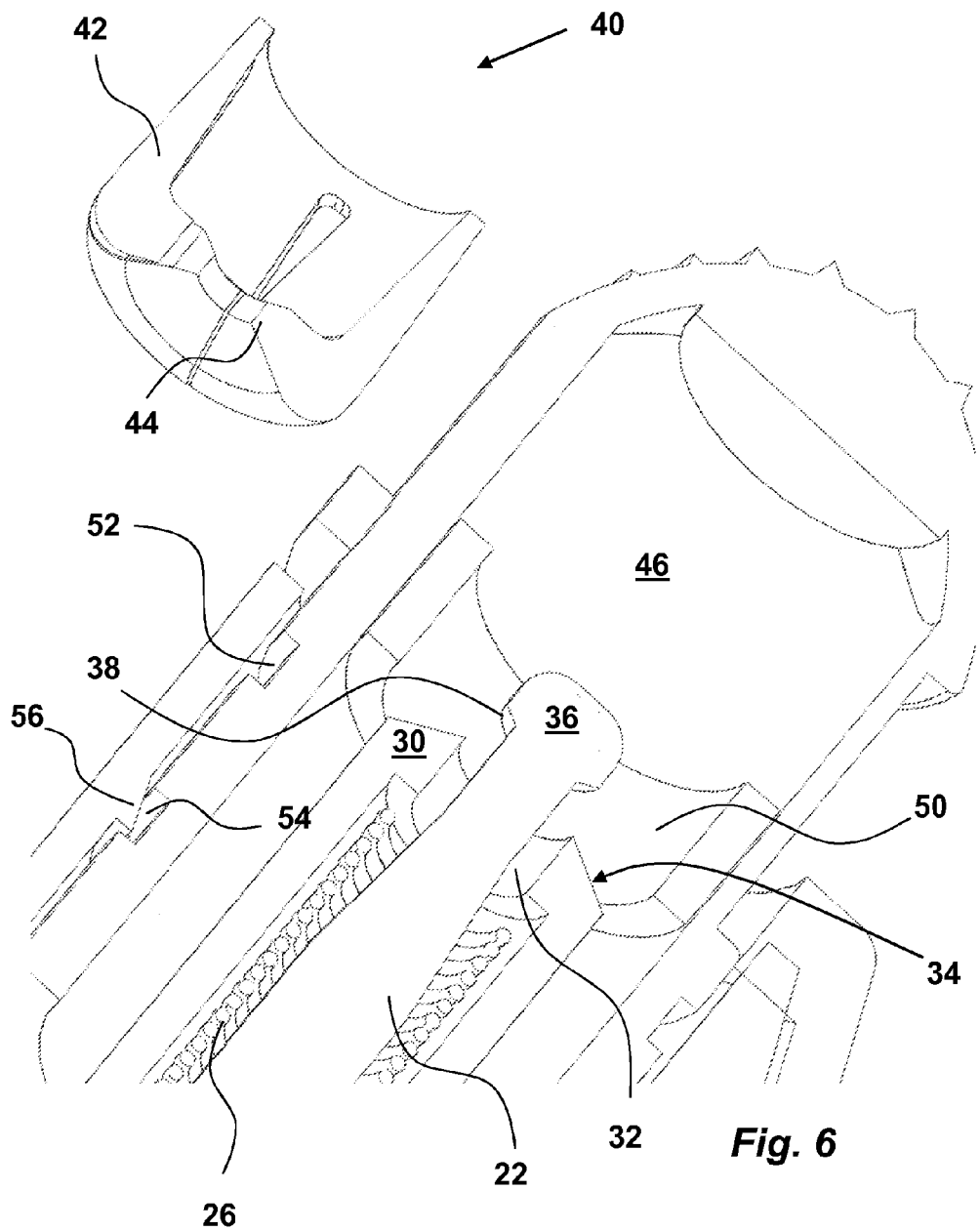
FIG. 6 is a detailed view of a distal part of the device of FIG. 1, and FIGS. 7 a,b are detailed views of the device of FIG. 1.
Figure 7A:
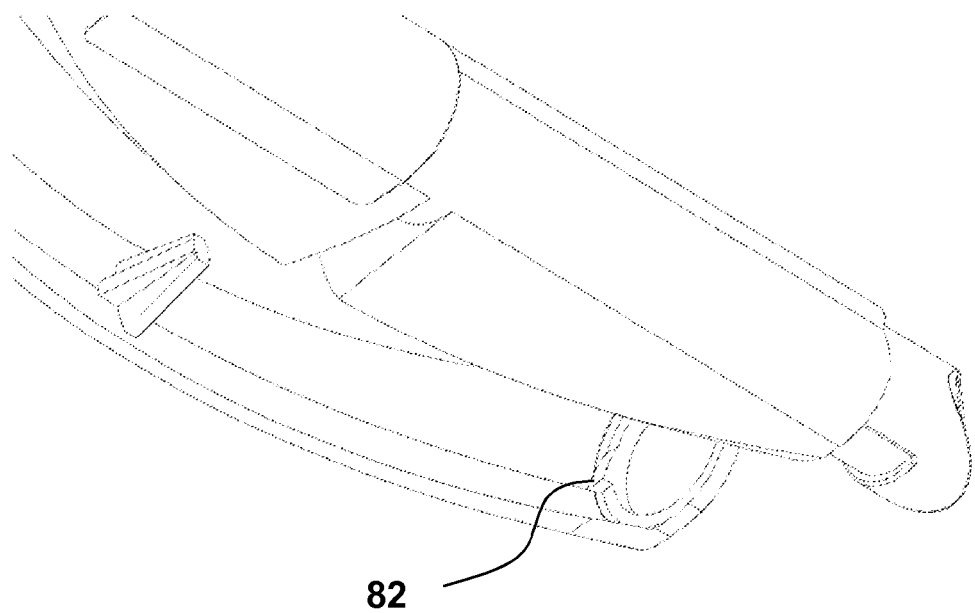
Figure 7B:
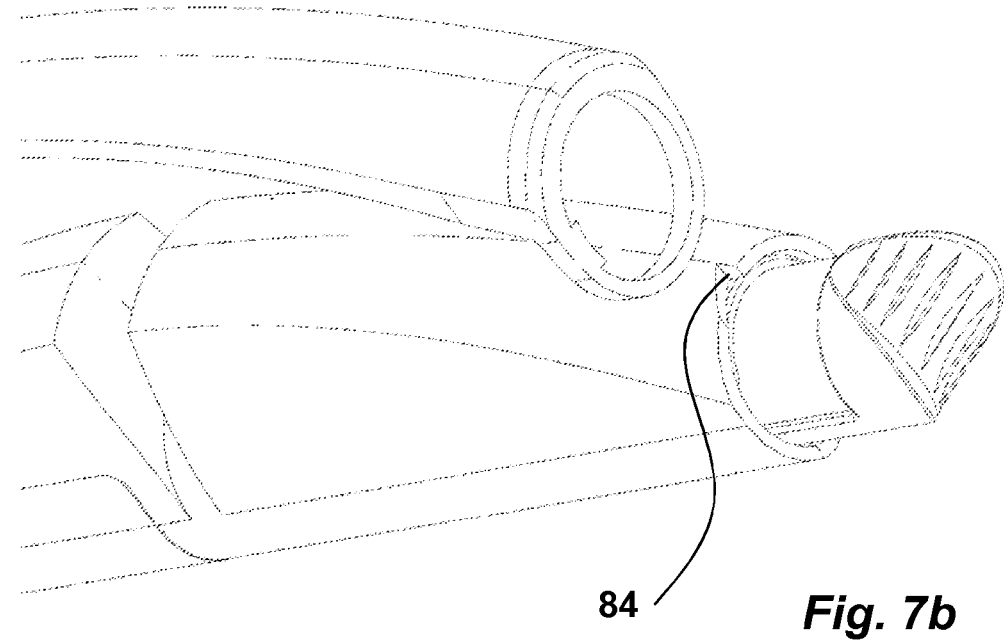

The hold and release means of the exemplary embodiment is shown in FIGS. 3, 4 and 6; comprises a lock member 40 having flexible arms 42, wherein each flexible arm is provided with a radial inwardly directed ledge 44. The distal end of the plunger rod 22 is arranged with an enlargement 36, providing a proximally directed annular ledge 38. The lock member 40 is arranged in contact with the distal end of the plunger rod 22 such that the radial inwardly directed ledges 44 are in contact with the annular ledge 38 of the enlargement 36 of the plunger rod, thus holding the drive means in the pre-tensioned state, FIGS. 2 and 6.

In the exemplary embodiment, as shown in FIGS. 1-5, the grip member is in the form of an elongated arc-shaped rib 64 extending in the longitudinal direction of the device and is rotatably attached to the housing, and the actuation means is in the form of an actuation button 46. The proximal end of the grip member is arranged with a ring portion 66 that surrounds the proximal neck portion of the housing. The distal end of the grip member is also arranged with a ring portion 68 that surrounds the actuation button 46. The rib 64 displays an arc-shape extension as seen in the transversal direction of the device. The housing 10 is designed such that the first surface part 74 thereof generally follows the curvature of said rib when in the rest position and that the second surface part 76 thereof which is positioned generally 180 degrees in relation to the first surface part 74 and which is generally parallel with the longitudinal axis of the device, creates a pre-determined distance to said rib when the rib is in the operation position. The support member 78 of the rib is in the form of a pin attached to the inner surface of the rib 64 and projects in a direction transversal to the longitudinal axis of the device. The first surface part 74 of the housing 10 is further arranged with a cut-out 80 for accommodating the support member when the grip member is in the rest position. The grip member is further arranged with limiting means arranged to co-act with corresponding limiting means of the housing such that said rib can only be turned in one direction and generally 180 degrees between said rest position and said operation position. In the exemplary embodiment, the limiting means is a first stop ledge 82, FIG. 7a, attached to the proximally directed surface of the distal ring portion 68 and the corresponding limiting means is a corresponding second stop ledge 84, FIG. 7b, arranged on the distal end surface of the housing. The two ledges 82, 84 thus provide a rotational stop in one direction so that the grip member 62 may only be rotated in one direction as will be described below.

In the exemplary embodiment, the actuation means is interactively connected to the rib and to the housing, and wherein said actuation means is movable between a locked position in which said actuation means and said housing are interlocked to each other by actuation interlocking means when the rib is in the rest position, and a released position in which said actuation means are released from said housing when the rib is in the operation position, such that the actuation means can be activated for interacting with the hold and release means and thereby release the drive means from the pre-tensioned state. In the exemplary embodiment, the actuation means comprises the actuation button 46 arranged surrounding the lock member 40 and the tubular part 24. The actuation button 46 being in the form of a generally tubular actuation button and having a distal end protruding through the distal end 48 of the housing 10. The inner surface of the actuation button is arranged with an annular ring 50 which is in contact with the outer surfaces of the arms 42 of the lock member 40. The actuation button is connected to the housing by two circumferential grooves 52, 54 on the outer surface of the actuation button and by a protrusion 56 on the inner surface of the housing, FIG. 6. The actuation button is further interactively connected to the housing by the actuation interlocking means. In the exemplary embodiment, the actuation interlocking means being a proximally directed pin 58, FIG. 3, and an annular ledge 60, FIG. 4, on the inner surface of the housing. The actuation button is also interactively connected to the rib by a track groove 72 arranged on the outer surface of the actuation button and by a guide member 70 in the form of an inwardly protruding ledge, FIG. 4, arranged on the inner surface of the ring portion 68. Said guide member 70 being arranged to fit into the track groove 72 of the actuation button 46, and wherein the track groove 72 has a certain extension in both the longitudinal direction as well as in the circumferential direction. As seen in FIG. 6, the protrusion 56 on the inner surface of the housing fits into one of the circumferential grooves for preventing the actuation button 46 to be moved in the distal direction out of the housing 10 but allowing rotation of the actuation button in relation to the housing as will be described.

The device further comprises a protective cap 16 releasibly attached to the proximal end of the housing, operably connected to said rib and movable between a closed position in which said protective cap and said rib are interlocked to each other by appropriate interlocking means when said rib is in the rest position, and an open position in which said protective cap is removed such that the rib can be moved from the rest position to the operation position. The proximal end 12 of the housing is arranged with a neck portion arranged with engagement means as e.g. thread segments on its outer surface and the protective cap 16 is releasably attached to the neck portion by appropriate engagement means.

It is also to be understood that the protective cap 16 may also be releasibly attached to the proximal end of the housing and operably connected to said rib, such that said protective cap and said rib are interlocked to each other when said rib is in the rest position and such that said protective cap and said rib are released from each other when said rib is in the operation position such that said cap can be removed.

The device of the exemplary embodiment is intended to function as follows. When the device is delivered to a user, the protective cap 16 is attached to the proximal end of the device and a medicament container 18 is placed inside the device. The grip member is in the rest position. The connection between the grip member and the actuation button 46 is such that in the rest position, the pin 58 of the actuation button 46 is in contact with the ledge 60 of the housing 10 so that the actuation button 46 cannot be depressed.

When a dose of medicament is to be delivered to the user, the protective cap 16 is removed and a medicament delivery member is either attached or exposed. The grip member is now turned about 180 degrees around the longitudinal axis of the device to the second surface part 76 and thus to the operation position, whereby the stop ledges 82, 84 ascertain that the grip member may only be rotated in one direction and about 180 degrees. As seen from FIG. 5 the grip size of the device increases due to that the transversal measure is increased by the rib 64 and thus the grip size becomes larger and the device becomes easier for a user to grip and hold. The rib is prevented from flexing in the radial direction by the support member 78 in contact with the second surface part 76.

The turning of the grip member has also caused a turning of the actuation button 46 because of the ledge 70 acting on a side edge of a groove 72 on the actuation button, whereby the proximally directed pin 58 of the actuation button 46 is moved out of contact with the ledge 60 of the housing. The actuation button can thus be pressed in the proximal direction which also is enabled by the ledge 70 moving in the longitudinal direction in the groove 72 of the actuation button 46, which movement of the actuation button causes the annular ring 50 of the actuation button also to move in the proximal direction in relation to the lock member 40 such that the ring 50 is moved out of contact with the arms 42. This in turn enables the arms 42 to flex radially outwards because of the proximal ends of the arms 42 coming in contact with the bevelled distal surface 34 of the tubular part 24 of the housing 10. The plunger rod 22 is now free to move and is urged in the proximal direction by the compression spring 26, whereby the stopper 20 is forced in the proximal direction inside the medicament container 18 and a dose of medicament is expelled through the medicament delivery member.

When the user presses the actuation button 46 the protrusions 56 on the inner surface of the housing are moved into the second annular groove 54 of the actuation button 46 such that when the user then releases the actuation button 46, it becomes locked in the depressed position. The protective cap 16 can now be returned onto the proximal end of the device for avoiding e.g. accidental needle sticks if the medicament delivery member is an injection needle. Then the grip member 62 may be returned to its initial position and the device may be discarded.

The groove 72 of the actuation button has such an extension in the circumferential direction so that only the button may be rotated for actuating the device. This gives an option not to use the grip member in certain instances if the user is capable of turning the actuation button and/or can hold the device in a good grip without the aid of the grip member.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
an elongated housing having opposite distal and proximal ends and opposite first and second surface parts, wherein the first surface part includes an elongated arc-shape, and the second surface part is substantially parallel to a longitudinal axis of the device;
a grip member connected to the elongated housing and movable between a rest position, in which the device has a predetermined grip size, and an operation position for injecting a medicament, in which the predetermined grip size is increased;
wherein the grip member comprises an elongated arc-shaped rib extending in a longitudinal direction of the device and rotatably attached to the housing; when the rib is in the rest position, the first surface part and an inner surface of the rib abut each other such that the predetermined grip size of the device is a distance between the second surface part and an outer surface of the rib; and when the rib is in the operation position, the rib is opposite to the first part surface such that the increased predetermined grip size is a distance between the outer surface of the rib and the first surface part.

2. The medicament delivery device of claim 1, wherein the rib includes a limiting device configured for co-acting with a corresponding limiting device of the housing.

3. The medicament delivery device of claim 2, wherein the housing is configured for accommodating a medicament container.

4. The medicament delivery device of claim 3, further comprising an actuator and a driver interactively connected to each other, wherein the driver is arranged within the elongated housing and configured for acting, upon activation of the actuator, on a movable stopper inside the medicament container for expelling a dose of medicament.

5. The medicament delivery device of claim 4, further comprising a hold and release device interactively connected to the driver, for holding the driver in a pre-tensioned state, and to the actuator, such that when the actuator is activated, the hold and release device releases the driver from the pre-tensioned state.

6. The medicament delivery device of claim 5, wherein the actuator is interactively connected to the rib and to the housing, and the actuator is movable between a locked position, in which the actuator and the housing are interlocked to each other by an interlock when the rib is in the rest position, and a released position, in which the actuator is released from the housing when the rib is in the operation position, such that the actuator can be activated for interacting with the hold and release device and thereby release the driver from the pre-tensioned state.

7. The medicament delivery device of claim 2, wherein the rib comprises a support member configured for contacting the housing for preventing a radial movement of the rib when the rib is in the operation position and the device is gripped by a user.

8. The medicament delivery device of claim 2, wherein the medicament delivery device is an injection device.

9. The medicament delivery device of claim 2, further comprising a protective cap releasably attached to the proximal end of the housing, operably connected to the rib, and movable between a closed position, in which the protective cap and the rib are interlocked to each other when the rib is in the rest position, and an open position, in which the protective cap is removed such that the rib can be moved from the rest position to the operation position.

10. The medicament delivery device of claim 2, further comprising a protective cap releasably attached to the proximal end of the housing and operably connected to the rib, such that the protective cap and the rib are interlocked to each other when the rib is in the rest position and such that the protective cap and the rib are released from each other when the rib is in the operation position, such that the cap can be removed.

11. The medicament delivery device of claim 1, wherein the housing is configured for accommodating a medicament container.

12. The medicament delivery device of claim 11, further comprising an actuator and a driver interactively connected to each other, wherein the driver is arranged within the elongated housing and configured for acting, upon activation of the actuator, on a movable stopper inside the medicament container for expelling a dose of medicament.

13. The medicament delivery device of claim 12, further comprising a hold and release device interactively connected to the driver, for holding the driver in a pre-tensioned state, and to the actuator, such that when the actuator is activated, the hold and release device releases the driver from the pre-tensioned state.

14. The medicament delivery device of claim 13, wherein the actuator is interactively connected to the rib and to the housing, and the actuator is movable between a locked position, in which the actuator and the housing are interlocked to each other by an interlock when the rib is in the rest position, and a released position, in which the actuator is released from the housing when the rib is in the operation position, such that the actuator can be activated for interacting with the hold and release device and thereby release the driver from the pre-tensioned state.

15. The medicament delivery device of claim 1, wherein the rib comprises a support member configured for contacting the housing for preventing a radial movement of the rib when the rib is in the operation position and the device is gripped by a user.

16. The medicament delivery device of claim 1, wherein the medicament delivery device is an injection device.

17. The medicament delivery device of claim 1, further comprising a protective cap releasably attached to the proximal end of the housing, operably connected to the rib, and movable between a closed position, in which the protective cap and the rib are interlocked to each other when the rib is in the rest position, and an open position, in which the protective cap is removed such that the rib can be moved from the rest position to the operation position.

18. The medicament delivery device of claim 1, further comprising a protective cap releasably attached to the proximal end of the housing and operably connected to the rib, such that the protective cap and the rib are interlocked to each other when the rib is in the rest position and such that the protective cap and the rib are released from each other when the rib is in the operation position, such that the cap can be removed.

\* \* \* \* \*